United States Patent [19]

Dean et al.

[11] 3,993,654

[45] Nov. 23, 1976

[54] PREPARATION OF TETRACHLOROPYRIDINE

[75] Inventors: Norman LeRoy Dean, Lake Jackson; Wallace Eldon Embrey, Freeport; John Thomas Marshall, Lake Jackson, all of Tex.

[73] Assignee: The Dow Chemical Company, Midland, Mich.

[22] Filed: May 16, 1974

[21] Appl. No.: 470,473

[52] U.S. Cl. .......................................... 260/290 HL
[51] Int. Cl.² .................................... C07D 213/61
[58] Field of Search ...................... 260/290, 290 HL

[56] References Cited
OTHER PUBLICATIONS

Schroeter et al., Berichte, vol. 65, pp. 432–445, (1932).
Schroeter et al., Berichte, vol. 71, pp. 671–677, (1938).
Oparina, Berichte, vol. 64, pp. 575–576, (1931).
Bak, J. Org. Chem., vol. 21, pp. 797–798, (1956).

*Primary Examiner*—G. Thomas Todd
*Attorney, Agent, or Firm*—Walter J. Lee

[57] ABSTRACT

Tetrachloropyridine is prepared by heating pentachloropyridine in an aqueous medium under pressure, with agitation, in the presence of a particulate oxidizable metal, e.g., zinc and a hydrogen-producing acid, e.g., hydrogen chloride. The tetrachloropyridine is then conveniently extracted with an inert, water-immiscible solvent, e.g., a halogenated hydrocarbon.

2 Claims, No Drawings

PREPARATION OF TETRACHLOROPYRIDINE

BACKGROUND OF THE INVENTION:

Tetrachloropyridine is an important commercial product useful in preparation of insecticide formulations. It has been prepared commercially by heating pentachloropyridine in an alchohol medium (e.g., iso-butanol and water azeotropic mixture) in the presence of zinc and HCl. The commercial preparation in alcohol normally results in maximum yields and conversions of about 78 and 80 percent, respectively, and side-products tri- and di-chloropyridine are wasted.

The prior process which employs alcohol as a reaction medium has several deficiencies which are best avoided, if possible. One deficiency is that alcohol is flammable and toxic and presents hazards to persons working on or near the process. Another deficiency is that it is virtually impossible in large commercial operations to prevent spilled or escaped alcohol from polluting the air or nearby drainage conduits. A further deficiency is that alcohol is miscible, to a significant extent, with the starting material (pentachloropyridine or PCP), with the side-products, and with the product of the reaction (sym-tetrachloropyridine or s-TCP). The metal salt, e.g., $ZnCl_2$, which is produced as a by-product is more easily put to good use if it is not contaminated with alcohol. The side-products which are made in the process (such as, di- and tri-chloropyridine) and residual unreacted PCP are difficult to completely extract from alcohol.

The prior process referred to above can be graphically represented as follows:

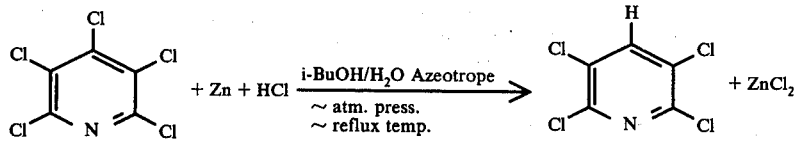

The embodiment illustrated here shows that pentachloropyridine (m.p. 124° C) is converted to symmetrical-tetrachloropyridine (s-TCP) by reacting with Zn and HCl in iso-butanol carrier at about atmospheric pressure and at reflux temperature. $ZnCl_2$ is formed and other by-products (not shown) which are formed are small amounts of unsymmetrical-tetrachloropyridine, trichloropyridine, and dichloropyridine. Pentachloropyridine is partly soluble in iso-butanol (about 31.4 gms./100 gms. of i-BuOH). Since the starting material (PCP) and the reaction products are somewhat soluble in the alcohol, complete extraction and separation of these materials are difficult and inefficient.

It can be readily understood that, aside from the need to obtain better-yields of sym-tetrachloropyridine and conversions in a commercial process, it is highly desirable and beneficial to provide a safer, more economical process, reduce the contaminants of the product and by-product, avoid environmental pollution, and to conserve hydrocarbons.

It is an object of the present invention to obtain better yields and conversions than are obtained by the prior method of using an alcohol reaction medium.

It is another object to provide a safer process than when alcohol is employed.

Another object is to provide a process which does not have the pollution problems associated with the use of alcohol and to obtain products and side-products which are not contaminated with alcohol.

Yet another object is to provide a process which conserves hydrocarbon values by avoiding the use of alcohol as a reaction medium.

These and other objects are obtained by the present invention as described hereinafter.

It has now been found that by employing an aqueous reaction medium, rather than an alcohol reaction medium, that a safer, ecologically beneficial process is obtained which, surprisingly and unexpectedly gives better conversions and better yields to the desired TCP and less side products, such as di- or trichloropyridine. The metal salt (e.g., $ZnCl_2$) which is formed is more easily purified than when contaminated with alcohol, thus is more easily and economically put to further use, such as in preparing particulate metal for recycling in the process.

SUMMARY OF THE INVENTION

Tetrachloropyridine is prepared by heating, in an aqueous medium, pentachloropyridine, a hydrogen-donating acid, and an oxidizable metal which combines readily with reactive chlorine, said heating being done at a temperature of about 110° C or greater, preferably at a temperature at which the pentachloropyridine is molten, and at a pressure which is at least about autogenous.

DETAILED DESCRIPTION OF THE INVENTION

In general, the invention is practiced by heating, with agitation, in a closed vessel, particulate pentachloropyridine, a fluid hydrogen-donating acid, and a particulate oxidizable metal in an aqueous medium or carrier. The vessel is closed in order that the desired temperature can be reached by confining the water under at least about autogenous pressure.

The hydrogen which is supplied by the hydrogen-donating acid is very active and can be considered to be nascent hydrogen. This active hydrogen replaces the chlorine in the fourth position on the PCP which has preferentially reacted with the oxidizable metal, e.g., zinc. If there is an overabundance of this nascent hydrogen present, or a deficiency of the metal, then the hydrogen tends to form $H_2$ which is subsequently released from the reaction mixture.

The pentachloropyridine should be in particulate and dispersed form during the reaction and should be stirred or agitated in order to prevent the particles, when they become softened or molten, from agglomerating. The PCP may be particulated and dispersed in the aqueous medium or carrier prior to being heated to a softened or molten condition such as by grinding or shearing or may be added to the aqueous medium in the reaction vessel and stirred and heated at the same time, in which case a strong agitation, such as by a stirrer having a power input of at least about 0.005 horsepower/gallon, preferably at least about 0.015 horsepower/gallon, has been found to be particularly advantageous.

If it is desired to particulate and disperse non-molten PCP in the aqueous medium prior to being introduced into the reaction vessel, then any suitable high-intensity agitator, such as a Kenics mixer or a high-shear recycling pump can be employed.

The temperature at which the PCP is reacted with the hydrogen-producing acid and the oxidizable metal may be from about 110° C on up to 160° C or more. Since the reaction works best at temperatures at which the PCP is molten, then a temperature of at least about 124° C is preferred, most preferably about 124°–160° C. Temperatures higher than 160° C may be used, but such higher temperatures create higher autogenous pressure which require more expensive vessels to contain such pressures. Higher temperatures and pressures are more easily accomodated in a tube-type or coil reactor, useful in continuous flow reactions, having intermittent acid feeders along its length.

The reaction pressure is at least autogenous since the reaction temperature is above the boiling point of water. Pressures greater than autogenous may be generated by pressuring in the hydrogen-producing acid after the other ingredients in the reaction vessel have been brought up to reaction temperature.

The reaction time may vary over a wide range depending on the temperature, the choice of oxidizable metal, the choice of hydrogen-donating acid, and the ratio of ingredients to each other. Reaction times generally are highly dependent on the rate of addition of the acid which in turn is dependent on the rate at which the nascent hydrogen is produced and utilized. The rate of HCl additiona, then, should be as slow as is practical for efficient operation and at a rate commensurate with the hydrogen utilization. The hydrogen utilization is best monitored by taking samples of the reactor vapors and analyzing for the presence of $H_2$ (molecular hydrogen). If $H_2$ is present in the reactor vapors, then the acid is being added too fast and thus, the oxidizable metal is not being utilized most effectively. Once it is learned what the hydrogen utilization will be for a given set of conditions then the optimum rate of acid addition, including controlling the heat of reaction, can be easily determined. There is an exotherm which is easily controlled in small reactors and tube or coil reactors, but which, in large stirred vessels, should be regulated by heat transfer and by rate of acid addition. Ordinarily, HCl addition time of from about 0.5 to about 5.0 hours are employed, with times of about 1.0 to about 4.0 hours being preferred.

The hydrogen-donating acid (alternately called "hydrogen-producing acid") may be a hydrogen halide, such as HCl, HBr, HI, or HF, or may be $HNO_3$, $H_3PO_4$, $H_2SO_4$, ROOH, where R is a lower alkyl group of from 1 to about 8 carbon atoms (e.g., acetic acid or hexanoic acid), or any acid which releases nascent or reactive hydrogen upon being reacted with an oxidizable metal. The most preferred acid is HCl; it does not introduce anions which are different from the chlorine being removed from the PCP. The acid may be in aqueous solution or may be essentially anhydrous, depending on whichever form is most convenient or feasible under the circumstances in which it is to be used. It is generally preferred to use an acid which is essentially anhydrous in order that additional quantities of water in the reactor can be avoided.

The oxidizable metal is preferably zinc because it is found to give best results and because it forms metal salts which are relatively easy to recover from the aqueous reaction medium. Other oxidizable metals may be used however, such as Fe, or Mg.

In one embodiment of the invention, PCP is dispersed in water in particulate, non-molten form by employing high-intensity agitation, such as by a Kenics mixer or by a recycle pump. The so-formed slurry is fed into a reaction vessel and particulate oxidizable metal is added. The vessel is sealed and the mixture is stirred and heated until the mixture reaches the desired temperature, which is preferably at least the melting point of the PCP. The hydrogen-producing acid is pressured into the vessel (as stirring is continued) at a rate commensurate with the efficient utilization of the nascent hydrogen produced. At the completion of the reaction, the chloropyridines are taken up in an inert, water-immiscible solvent (e.g., a chlorinated hydrocarbon) and the metal salt is recovered from the aqueous phase.

Another suitable method is that of adding molten PCP to a heated slurry of particulate metal in $H_2O$ and, with agitation to disperse the PCP, is brought to the desired reaction temperature in the sealed vessel and introduction the the hydrogen-donating acid is commenced and continued at the appropriate rate until the reaction is completed.

In another embodiment the PCP, water, and Zn are charged to the reactor. The reactor is sealed and the mixture is heated, with strong agitation, until the PCP is sufficiently heated, preferably molten. The acid is then pressured into the reactor at a rate which is commensurate with efficient utilization of the nascent hydrogen formed.

For best results in obtaining high conversion of the PCP charged to the reactor, the mole ratio of oxidizable metal to PCP should preferably be in the range of about 1.0 to 1.4, most preferably about 1.1 to 1.3. The process will operate with more or less of the metal, but if less is used there may not be enough to react with all the PCP; if more is used, there is an increased tendency to cause attack of the chlorine on the PCP in positions other than the fourth position, thereby producing di-, and trichloropyridines.

The ratio of hydrogen-producing acid to oxidizable metal should, preferably, be a mole ratio of about 1.0 to about 1.4 for acids having one hydrogen atom per anion. For acids having two hydrogen atoms per anion, then the mole ratio should be, preferably, about 0.5 to about 0.7 and for acids having three hydrogens per anion, about 0.3 to about 0.5.

The amount of water used as carrier for the reaction can vary over a wide range. Ordinarily, the weight ratio of water to PCP is at least about 0.4 and can be 4.0 or more, with the ratio of 1.0 to 3.0 being preferred; most preferably a ratio of about 1.4 to 2.0 is preferred. Essentially, there should be enough water to help disperse the PCP and to take up the metal salt formed. Having a large excess of water merely adds to the amount of energy and equipment size required to operate the process.

EXAMPLE 1–6

In the following examples (charted in Table I) water, PCP, and particulate Zn were charged into the reactor. The reactor was closed and the mixture was heated and stirred in order to melt and disperse the PCP. Autogenous pressures were developed. Then HCl was pressured into the reactor at a controlled rate. Following the reaction period, the chloropyridines were extracted from the aqueous medium with perchloroethylene. The $ZnCl_2$ was recovered from the aqueous phase. These examples illustrate the effect, primarily, of varying the ratio of Zn/PCP.

1–14 above. Examples 15–19 show the effect, primarily, of varying the ratio of HCl/Zn.

TABLE I

|  | RUN NUMBER | | | | | |
|---|---|---|---|---|---|---|
|  | 1 | 2 | 3 | 4 | 5 | 6 |
| REACTANT RATIOS | | | | | | |
| Zn/PCP mole ratio | .25 | .51 | 1.00 | 1.30 | 1.60 | 1.90 |
| HCl/Zn mole ratio | 7.21 | 3.61 | 1.79 | 1.37 | 1.26 | 1.50 |
| HCl/PCP mole ratio | 1.80 | 1.84 | 1.79 | 1.78 | 2.02 | 2.85 |
| $H_2O$/PCP wt. ratio | 3.00 | 3.05 | 3.00 | 3.00 | 3.00 | 2.99 |
| RUN CONDITIONS | | | | | | |
| Reaction temp. °C. | 131 | 131 | 132 | 130 | 131 | 132 |
| Reaction press., psig. | 40 | 40 | 40 | 40 | 40 | 40 |
| Agitation, approx. power input, hp/gal | .04 | .04 | .04 | .04 | .04 | .04 |
| HCl addn. rate, moles/hr. | 3.41 | 3.41 | 3.41 | 3.41 | 3.88 | 4.38 |
| HCl addn. time, min. | 127 | 127 | 126 | 125 | 125 | 156 |
| Conversion of PCP, % | 18.3 | 40.6 | 78.9 | 88.7 | 98.2 | 99.6 |
| Yields to $Cl_2Pyr$ | 0 | .38 | 1.11 | 2.83 | 3.89 | 13.0 |
| Yield to $Cl_3Pyr$ | 1.8 | 2.03 | 3.29 | 4.43 | 7.54 | 13.5 |
| Yield to $Cl_4Pyr$ | 98.2 | 97.6 | 95.6 | 92.7 | 88.6 | 73.5 |

EXAMPLES 7–14

These examples, shown in Table II, were made in essentially the same manner as in Examples 1–6 above, except that the ratio of $H_2O$/PCP was varied.

EXAMPLES 15–19

These examples, shown in Table III, were done essentially in accordance with the procedure for Examples

EXAMPLES 20–26

These examples, shown in Table IV, were prepared essentially in accordance with the procedure of Examples 1–19 above, except that Runs 20–23 show the effect, primarily, of varying the agitation and Runs 24–26 show the effect, primarily, of varying the rate of HCl addition.

TABLE II

|  | RUN NUMBER | | | | | | | |
|---|---|---|---|---|---|---|---|---|
|  | 7 | 8 | 9 | 10 | 11 | 12 | 13 | 14 |
| REACTANT RATIOS | | | | | | | | |
| Zn/PCP mole ratio | 1.30 | 1.30 | 1.30 | 1.30 | 1.30 | 1.30 | 1.30 | 1.30 |
| HCl/Zn mole ratio | 1.12 | 1.14 | 1.43 | 1.41 | 1.20 | 1.44 | 1.19 | 1.41 |
| HCl/PCP mole ratio | 1.46 | 1.47 | 1.86 | 1.83 | 1.56 | 1.86 | 1.55 | 1.84 |
| $H_2O$/PCP wt. ratio | 0.49 | 1.00 | 1.00 | 1.50 | 2.00 | 2.00 | 3.00 | 3.00 |
| RUN CONDITIONS | | | | | | | | |
| Reaction temp. °C | 132 | 127 | 130 | 130 | 130 | 130 | 130 | 130 |
| Reaction press., psig. | 44 | 40 | 40 | 40 | 40 | 40 | 49 | 40 |
| Agitation, approx. power input, hp/gal | 0.038 | 0.038 | 0.038 | 0.038 | 0.038 | 0.038 | 0.038 | 0.038 |
| HCl addn. rate, moles/hr. | 4.74 | 4.74 | 4.74 | 4.74 | 4.74 | 4.74 | 4.74 | 4.74 |
| HCl addn. time, min. | 256 | 177 | 206 | 154 | 106 | 127 | 82 | 90 |
| Conversion of PCP, % | 86.1 | 91.0 | 91.2 | 92.5 | 91.1 | 93.5 | 93.1 | 91.3 |
| Yields to $Cl_2Pyr$ | .86 | 2.12 | 1.6 | 1.81 | 2.22 | 3.66 | 4.8 | 4.03 |
| Yield to $Cl_3Pyr$ | 9.56 | 7.21 | 7.4 | 5.46 | 5.50 | 7.61 | 7.6 | 6.4 |
| Yield to $Cl_4Pyr$ | 89.6 | 90.7 | 91.1 | 92.7 | 92.3 | 88.7 | 87.6 | 89.6 |

TABLE III

|  | Run Number | | | | |
|---|---|---|---|---|---|
|  | 15 | 16 | 17 | 18 | 19 |
| REACTANT RATIOS | | | | | |
| Zn/PCP mole ratio | 1.30 | 1.30 | 1.30 | 1.30 | 1.30 |
| HCl/Zn mole ratio | 0.77 | 0.90 | 1.10 | 1.41 | 2.01 |
| HCl/PCP mole ratio | 1.00 | 1.17 | 1.43 | 1.83 | 2.61 |
| $H_2O$/PCP wt. ratio | 1.50 | 1.50 | 1.50 | 1.50 | 1.50 |
| RUN CONDITIONS | | | | | |
| Reaction temp. °C. | 130 | 130 | 130 | 130 | 130 |
| Reaction press., psig. | 40 | 40 | 40 | 40 | 40 |
| Agitation, approx. power input, hp/gal. | 0.038 | 0.038 | 0.038 | 0.038 | 0.038 |
| HCl addn. rate, moles/hr. | 4.74 | 4.74 | 4.73 | 4.74 | 4.73 |
| HCl addn. time, min. | 84 | 99 | 121 | 154 | 220 |
| Conversion of PCP, % | 91.8 | 93.8 | 92.4 | 92.5 | 96.9 |
| Yields to $Cl_2Pyr$ | 1.46 | 1.34 | 4.64 | 1.81 | 2.21 |
| Yield to $Cl_3Pyr$ | 4.13 | 4.09 | 6.67 | 5.46 | 8.60 |
| Yield to $Cl_4Pyr$ | 94.4 | 94.6 | 88.7 | 92.7 | 89.2 |

TABLE IV

|  | RUN NUMBER | | | | | | |
|---|---|---|---|---|---|---|---|
|  | 20 | 21 | 22 | 23 | 24 | 25 | 26 |
| REACTANT RATIOS | | | | | | | |
| Zn/PCP mole ratio | 1.30 | 1.30 | 1.30 | 1.30 | 1.30 | 1.30 | 1.30 |
| HCl/Zn mole ratio | 1.21 | 1.20 | 1.41 | 1.21 | 1.21 | 1.41 | 1.38 |
| HCl/PCP mole ratio | 1.57 | 1.55 | 1.83 | 1.57 | 1.57 | 1.83 | 1.80 |

TABLE IV-continued

|  | \multicolumn{7}{c}{RUN NUMBER} |
|---|---|---|---|---|---|---|---|
|  | 20 | 21 | 22 | 23 | 24 | 25 | 26 |
| $H_2O$/PCP wt. ratio | 1.50 | 1.50 | 1.50 | 1.50 | 1.50 | 1.50 | 1.58 |
| RUN CONDITIONS | | | | | | | |
| Reaction temp. °C. | 130 | 130 | 130 | 128 | 130 | 130 | 130 |
| Reaction press., psig. | 40 | 40 | 40 | 40 | 40 | 40 | 40 |
| Agitation, approx. power input, hp/gal. | 0.005 | 0.015 | 0.038 | 0.076 | 0.038 | 0.038 | 0.038 |
| HCl addn. rate, moles/hr. | 4.74 | 4.74 | 4.74 | 4.74 | 2.64 | 4.74 | 7.40 |
| HCl addn. time, min. | 132 | 131 | 154 | 132 | 237 | 154 | 97 |
| Conversion of PCP, % | 86.5 | 91.1 | 92.5 | 93.2 | 95.5 | 92.5 | 82.5 |
| Yields to $Cl_2Pyr$ | 2.93 | 3.91 | 1.81 | 3.64 | 1.97 | 1.81 | 2.08 |
| Yield to $Cl_3Pyr$ | 5.84 | 7.24 | 5.46 | 6.60 | 4.93 | 5.46 | 6.30 |
| Yield to $Cl_4Pyr$ | 91.2 | 88.9 | 92.7 | 89.8 | 93.1 | 92.7 | 91.9 |

EXAMPLE 27–30

A series of runs were made to study the effect of varying the temperature. The runs were made essentially in accordance with the procedures employed in the previous examples; however, where the temperature was below the melting pt. of the PCP, the PCP is not molten. In these runs the mole ratio of Zn/PCP was about 1.30, the mole ratio of HCl/Zn was about 1.20–1.21, the mole ratio of HCl/PCP was about 1.55–1.57, and the weight ratio of $H_2O$/PCP was about 1.50.

The agitation (approx. power input) was 0.038 hp/gal., the HCl addition rate was about 4.74–4.75 moles/hr. and the HCl addition time was about 131–132 minutes.

The autogenous pressure which was generated was somewhat temperature-dependent and ranged from about 40 to about 85 psig. The data given below was obtained at the various temperatures shown:

Run 27. at 110° C, conversion of PCP was 86.3% with 87.3% of the products of conversion being TCP;
Run 28. at 120° C, conversion of PCP was 86.5% with 90.5% of the products of conversion being TCP;
Run 29. at 145° C, conversion of PCP was 94.1% with 91.2% of the products of conversion being TCP;
Run 30. at 156° C, conversion of PCP was 88.1% with 92.9% of the products of conversion being TCP.

EXAMPLE 31

(Comparative Example — Not an Example of the Present Invention)

Employing the same reactor as in the previous examples a run was made which did not use a reaction medium or solvent. PCP (4000 parts) was melted at 130° C and particulate zinc metal (260 parts) was added with stirring. Anhydrous HCl (190 parts) was added at the rate of about 172.7 parts per hour for a total of about 66 minutes, while keeping the reactor closed in order to prevent escape of any of the gases and vapors. The reaction mixture was then taken up in perchloroethylene and components were analyzed. There was obtained a conversion of the PCP of about 40.38% and the products of conversion contained about 86.57% tetrachloropyridine, about 10.57% dichloropyridine, and about 2.86% trichloropyridine.

EXAMPLE 32

(Comparative Example — Not Example of the Present Invention)

Several runs were made, in which the reaction medium was an azeotrope of $H_2O$/isobutyl alcohol, and in which various hydrogen-donating acids were employed. The reactions were made at reflux temperature at ambient pressure by the following procedure.

To a five-neck, 5-liter pot equipped with agitator and reflux consenser was added 1326 gms. of isobutanol and 166 gms. of water. This was brought to reflux temperature and 573 gms. of pentachloropyridine was dispersed in it. Then 195 gms. of Zn dust was dispersed in the mixture and the hydrogen-donating acid was added as fast as it was consumed. When the Zn dust was used up (as evidenced by its disappearance), the reaction was considered complete and the flow of acid was stopped. The results for each acid used are as shown below:

When anhydrous HCl was added, the reaction time was 65 minutes, the conversion of PCP was 87.6% and the yield of TCP was 71.7%.

When $H_2SO_4$ (50% aqueous solution) was added, the reaction took 250 ml. over 1.75 hrs., the conversion of PCP was 87.0% and the yield of TCP was 67.9%.

When $H_3PO_4$ (43% aqueous solution) was added, the reaction took 310 ml. over 1.5 hrs., the conversion of PCP was 86.9% and the yield of TCP was 70.9%.

When acetic acid was used, the reaction took 485 ml. of 50 wt. % acid and 220 ml. of 99.7 wt. % acid over a 6 hr. period, the conversion of PCP was 90.5% and the yield of TCP was 78.6%.

Even though the reaction medium employed in this example is not in accordance with the present invention, the runs in this example demonstrate that hydrogen-producing acids other than HCl are operable.

EXAMPLE 33

(Comparative Example — Not an Example of the Present Invention)

This example is to demonstrate the relative performance of Mg metal and Fe metal in comparison with Zn as the oxidizable metal.

Into a glass, laboratory reactor, equipped with means for heating, with stirrer, and with a reflux condenser was placed 800 gms. of dry isobutanol, about 251 gms. of PCP (1 mole), and about gram-mole of particulate metal. The mixture was stirred and heated at reflux temperature as conc. HCl was added dropwise over a period of time until the metal was all reacted. The following Table V gives the data.

TABLE V

| Metal Used | Gms. of Acid Added | Moles of HCl Used | Reaction Time, Hrs. | % Conv. of PCP | % Yield of TCP |
|---|---|---|---|---|---|
| Zn | 175 | 1.8 | 1.5 | 79.0 | 78.0 |
| Mg | 155 | 1.55 | 3.5 | 7.7 | 96.0 |
| Fe | 225 | 2.25 | 4.5 | 6.0 | 95.0 |

It can be seen then, that Mg and Fe are operable and give very high selectivity (yield) to TCP, but the conversion of PCP is quite low in comparison to Zn.

We claim:

1. In a process for preparing tetrachloropyridine by reacting pentachloropyridine, zinc, and HCl, the improvement which comprises carrying out said reaction in an aqueous medium at a temperature of at least 110° C under at least autogenous pressure, with the mole ratio of zinc/pentachloropyridine being in the range of about 1.0 to about 1.4, the mole ratio of HCl/zinc being in the range of about 0.1 to about 1.4, and the weight ratio of water/pentachloropyridine being at least about 0.4.

2. A process for preparing tetrachloropyridine which comprises heating and dispersing pentachloropyridine and zinc in an aqueous medium at a temperture of at least about 110° C and under at least autogenous pressure in a closed reactor for at least about 1 hour during which time HCl is added to the reactor and in which the weight ratio of water to pentachloropyridine is at least about 1.0, the mole ratio of zinc to pentachloropyridine is in the range of about 1.0 to about 1.4 and the mole ratio of HCl to zinc is in the range of about 1.0 to 1.4 and recovering tetrachloropyridine therefrom.

* * * * *